(12) United States Patent
Crawford et al.

(10) Patent No.: US 6,602,217 B2
(45) Date of Patent: Aug. 5, 2003

(54) FOOT DROP ASSISTANCE DEVICE

(75) Inventors: Michael K. Crawford, Houston, TX (US); James M. Killian, Houston, TX (US)

(73) Assignee: CK Partners, LLC, Houston, TX (US)

(*) Notice: Subject to any disclaimer, the term of this patent is extended or adjusted under 35 U.S.C. 154(b) by 20 days.

(21) Appl. No.: 09/981,004

(22) Filed: Oct. 16, 2001

(65) Prior Publication Data

US 2003/0073938 A1 Apr. 17, 2003

(51) Int. Cl.[7] .................................................. A61F 5/00
(52) U.S. Cl. ........................................................ 602/28
(58) Field of Search ............................. 602/28, 23, 29; 128/882; 36/11.5, 94

(56) References Cited

U.S. PATENT DOCUMENTS

| | | | |
|---|---|---|---|
| 2,663,294 A | * 12/1953 | Harrison | 602/28 |
| 2,928,191 A | * 3/1960 | Meltzer | 2/265 |
| 3,986,501 A | 10/1976 | Schad | |
| 4,329,982 A | 5/1982 | Heaneyt | |
| 4,566,447 A | * 1/1986 | Deis | 602/28 |
| 4,651,723 A | 3/1987 | Satoh | |
| 4,817,589 A | 4/1989 | Wertz | |
| 5,277,699 A | * 1/1994 | Williamson | 128/882 |
| 5,382,224 A | * 1/1995 | Spangler | 602/23 |
| 5,399,155 A | * 3/1995 | Strassburg et al. | 2/239 |
| 6,029,372 A | * 2/2000 | Pan | 36/11.5 |

* cited by examiner

*Primary Examiner*—Nicholas D. Lucchesi
*Assistant Examiner*—Fenn C Mathew
(74) *Attorney, Agent, or Firm*—Gary Bush; Andrews & Kurth, LLP

(57) ABSTRACT

A foot drop support arrangement including a leg member and a strap having a first end supportable between the big toe and an adjacent end and a removable attachment mechanism for attaching the second end to the leg member whereby a user can support his or her toe end of the foot from a leg support without necessity for a shoe and with ease of installation for a foot drop patient upon getting up after sleeping.

3 Claims, 2 Drawing Sheets

FOOT DROP ASSISTANCE DEVICE

BACKGROUND OF THE INVENTION

1. Field of the Invention

This invention relates generally to an apparatus, device, or arrangement which aids walking for a person having an ailment called foot drop. In particular, the invention relates to a device which provides assistance in lifting a foot of a foot drop patient, thereby enabling taking a step and walking. Still more particularly, the invention relates to a foot drop assistance device which enables a foot drop patient to easily and quickly install the device at any time, but especially upon getting out of bed at nighttime and to uninstall it when returning to bed.

2. Description of the Prior Art

Foot drop is the common name for a condition technically called dorsi-flexion weakness of the foot. The condition can be caused by neurological diseases and injuries in the brain, spinal cord and peripheral nervous system. Most brain causes result from strokes or cerebral injuries. Spinal cord causes include multiple sclerosis, degenerative lesions of the spinal cord and spinal cord injuries. Peripheral causes include spinal root damage from ruptured lumbar discs and injuries and inflammation of the lumbosacral nerve plexus to the leg. Sciatic and peroneal nerve injuries and inflammations can occur in the leg itself.

This invention relates to an apparatus for the alleviation of mild foot drop. Mild foot drop refers to a condition of foot drop which is uncomplicated by the presence of spasticity or severe lateral instability. It is confined to a disability of the anterio-posterior plane where the foot tends to hang in a plantar-flexed position which prevents or interferes with normal walking. An individual with mild foot drop requires the use of other muscles throughout the body to lift the dorsum portion of the foot. It requires muscles of the leg and the remainder of the torso. A person having mild foot drop is noticeable by the manner in which the foot is raised which appears to require great effort and requires the exertion of a directly upward force resulting in a limp. Because of the additional muscular effort which is needed to raise the foot during normal walking the individual becomes fatigued more than otherwise would be the situation in a person without foot drop.

Devices exist to dorsi-flex the foot while a foot drop patient is walking. A class of such devices, ankle-foot orthosis, involve a fixed support under the foot usually extending up over the ankle and calf to prevent the foot from flexing when lifting the leg to take a step. Some of these devices are fixed to a shoe and may include lateral support. Others are limited to the sole of the foot and a portion of the heel.

U.S. Pat. No. 3,986,501 to Schad shows a rigid vertical support which is curved and arched to conform about the rear of the calf and coupled to a V-shaped strap which is looped about a shoelace for alleviating foot drop. The arrangement requires a shoe, and a vertical leg apparatus and strap from a shoelace loop to the support on the leg. U.S. Pat. No. 4,329,982 to Heaney does not have a vertical support, but rather a leg attachment member and an elastomeric strap with means for attaching the support strap to the wearer's shoe. U.S. Pat. No. 4,817,589 to Wertz shows an arrangement with a low profile support member which conforms in shape to the leg above the ankle and a plurality of elastic straps attached between the support member and a shoe worn on the person's foot.

Many foot support devices require a shoe as part of the arrangement. A strap is coupled between a leg support device and the shoe. Such devices are clumsy to install on a foot drop patient in the middle of the night when the patient needs to get out of bed to go to the toilet, kitchen, or telephone and return to bed. Many foot drop patients cannot walk without supporting the front part of his/her foot, and installing prior devices by putting on a shoe and leg support, often in darkness, and then uninstalling the device on return to bed requires much effort and results in frustration.

3. Identification of Objects of the Invention

A primary object of the invention is to provide a support arrangement for a foot drop patient that eliminates the need for a shoe as part of the arrangement but provides support of the front part of the foot when walking from a bed to a toilet, kitchen, telephone or the like.

Another object of the invention is to provide a support arrangement for a foot drop patient that can be quickly installed upon getting out of bed, and quickly uninstalled when returning to bed.

Another object of the invention is to provide a support arrangement for a foot drop patient that is inexpensive, and can be quickly installed for effective support of the front part of the foot.

Another object of the invention is to provide a support arrangement for a foot drop patient that can be installed on the leg and foot, yet allow a shoe to be worn on the foot without attachment to the arrangement.

SUMMARY OF THE INVENTION

The objects identified above as well as other features and advantages of the invention are incorporated in a two piece arrangement which includes a leg support and a strap. The leg support is arranged and designed to be secured about the lower leg of the patient above the patient's ankle. A lower end of the strap is arranged and designed to be placed about or between the toes of the foot, preferably the big toe and the adjacent toe. The upper end of the strap and the leg support are cooperatively arranged and designed so that the upper end of the strap can be disconnectably fastened to the leg support with the result that the forward end of the foot is supported from the leg support so that it does not drop during walking. The arrangement may be used by the patient for sleeping with the leg support secured about the leg. The strap is placed nearby so that when the patient needs to get up, the strap is handy. The patient positions the lower end of the strap between the big toe and the adjacent toe and then fastens the upper part of the strap to the leg support such that the foot is prevented from dropping while walking. The patient is ready to immediately walk to the toilet or kitchen or another room as necessary. The patient is barefoot, that is without a shoe, yet has support for walking to overcome his foot drop condition. Upon returning to bed, the patient unfastens the upper part of the strap from the leg support and removes the lower part from the toes and returns to bed.

Alternatively, the arrangement may be used by the patient, after the strap is coupled between the toes and leg support, by wearing a shoe on the foot while the arrangement is in place.

BRIEF DESCRIPTION OF THE DRAWINGS

The objects, advantages, and features of the invention will become more apparent by reference to the drawings which are appended hereto and wherein like reference numbers indicate like parts and wherein an illustrative embodiment of the invention is shown, of which.

DETAILED DESCRIPTION OF THE PREFERRED EMBODIMENT OF THE INVENTION

Figure 1:
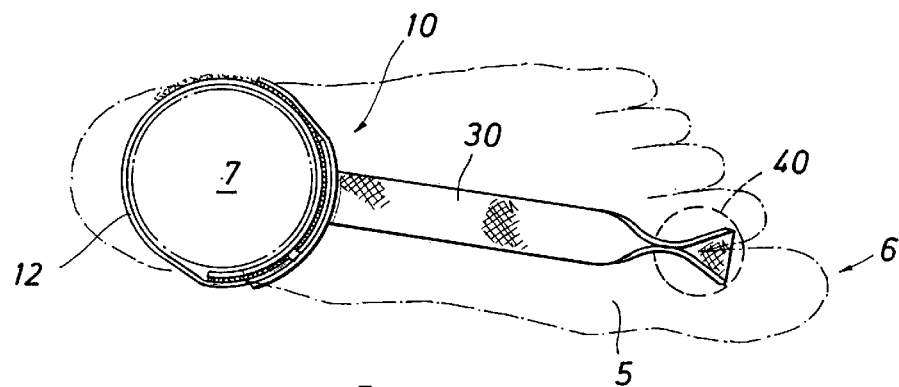
FIGS. 1 and 2 are top and side views of a foot drop support arrangement according to the invention, where the arrangement includes a leg support and a strap shown in an installed position between toes of a patient's foot and the leg support.
Figure 2:
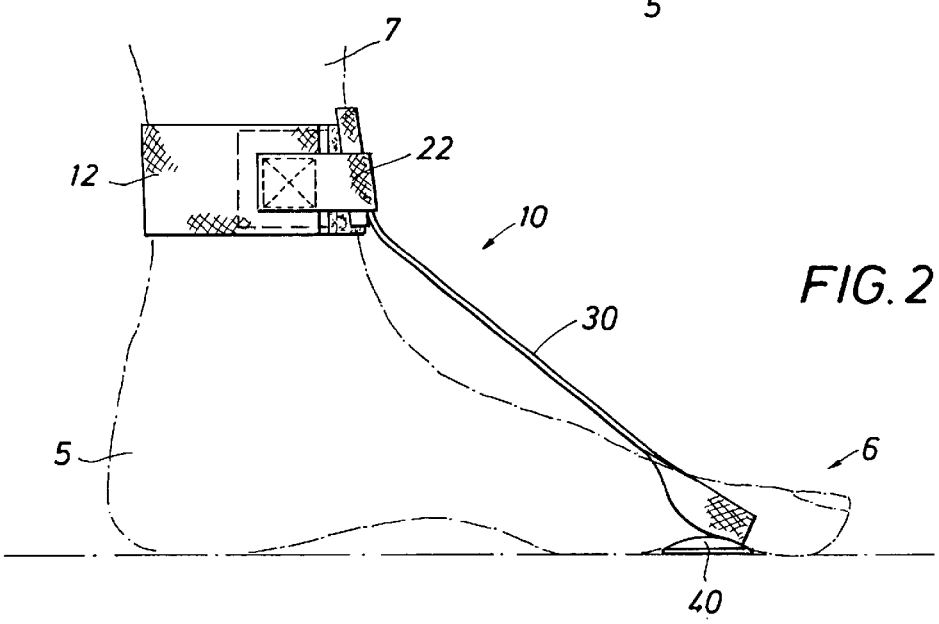

FIGS. 1 and 2 illustrate the foot drop support device 10 installed on a foot for supporting the toe end 6 of a foot 5 from a leg 7 of a foot drop patient. The device or arrangement 10 includes a leg member 12 which is arranged and designed for releasable attachment to a foot drop patient's leg 7 as shown in FIGS. 1 and 2. A strap 30 is arranged and designed to be inserted between the big toe and adjacent toe of the patient and to be releasably attached to the leg member 12, preferably at the front part of the leg member which faces the toe as shown in FIGS. 1 and 2.

Figure 3:
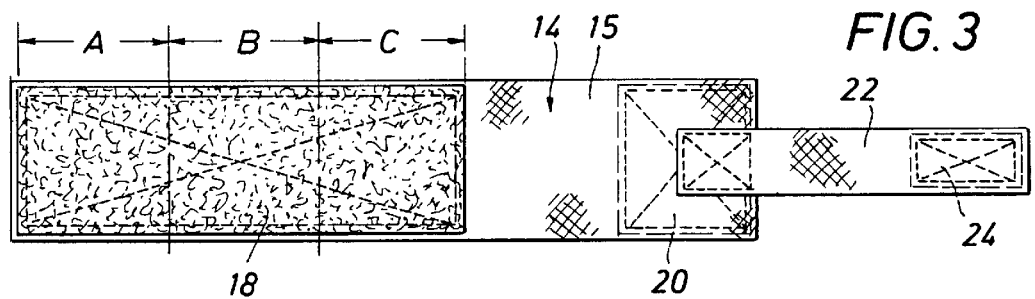
FIG. 3 is a top view of the leg support of the arrangement with a preferred fastening means in the form of loop and hook fastening strips for fastening the leg support about the lower leg including a primary rectangular fabric strip with a long rectangle of hook material sewn on one side and short rectangle of loop material sewn on the opposite side and with a closing tab attached to the end of the primary fabric strip with another loop rectangle secured to an end.
Figure 4:
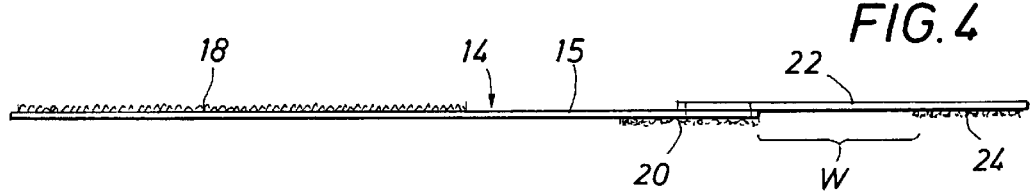
FIG. 4 is a side view of the leg support member showing hook material on one side of the primary fabric strip, loop material on the other side and the closing tab attached to an end of the primary fabric strip of the leg support.

As best seen in FIGS. 3 and 4, the preferred embodiment uses VELCRO® type fasteners which includes hook section 18 sewn to an outer side 15 of a fabric strip 14 and a loop section 20 sewn to an inner side 16 of the fabric strip 14. The terms "inner"and "outer" refer to the side of the strip that faces inward against the patient's leg 7 or faces away from the leg 7 when installed as a loop about the leg. A closing tab 22 is secured to the end of fabric strip 14 at which loop material 20 is secured. The closing tab 22 preferably has a section of loop material 24 affixed to its opposite end. Preferably a width w exists between the end of fabric strip 14 and the loop section 24 of closing tab 22 to overlap an end of strap 30 when removably secured to the hook portion 18 of leg member 12.

The leg member 12 is wrapped about the foot drop patient's leg 7 with the inner side 16 of fabric strap 14 next to the skin of the leg 7. The loop section 20 attaches to an end area A of hook portion 18, leaving a wide area B on the outer side 15 of fabric strip 14 available for attachment thereto of a loop section 32 of strap 30. After loop section 32 is removably secured to the "B" area of hook section 18 of leg member 12, as shown in FIG. 2, the closing tab 22 is wrapped about the fabric strip with the area W of the closing tab passing over the fabric side of loop section 32 and with the loop section 24 of closing tab 22 at least partially being pressed against a portion C of the hook area 18 of fabric strip 14, such that the end of the strap 30 is locked in place forming a strong attachment of the strap 30 to the leg member 12. The areas A, B and C referred to here are for purposes of illustration only. Physically, the hook section is preferably one piece of rectangular hook material sewn onto the outer side 15 of fabric 14.

Figure 5:
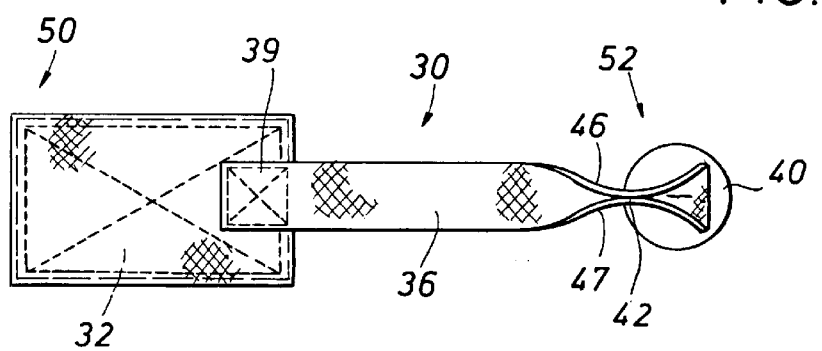
FIGS. 5, 6 and 7 are top, side and bottom views of the fabric strap of the arrangement of FIGS. 1 and 2 with a rectangle of loop material sewn to the bottom side of one end for attaching to a portion of the hook material of the leg member of FIGS. 3 and 4 and a button sewn to the other end where the fabric of the strap is folded over before connection of the button so that the folded over portion comfortably fits between the big toe and adjacent toe of the patient with the button adapted placed beneath such toes.
Figure 6:
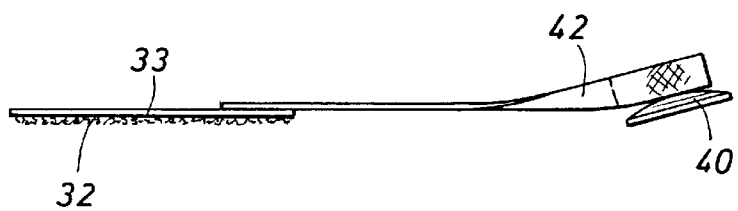
Figure 7:
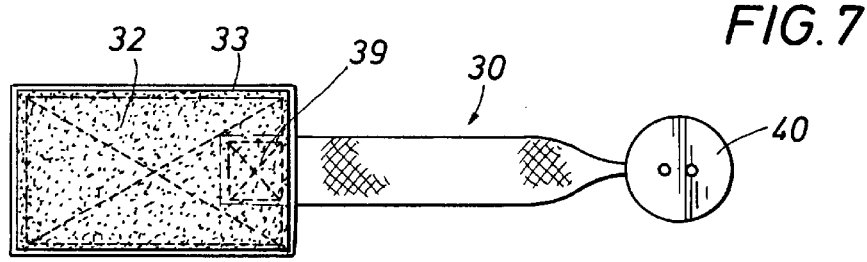

FIGS. 5, 6, and 7 show in top, side and bottom views the preferred embodiment of the strap 30. At the "leg" end 50 of the strap 30, a section of loop material 32 is sewn to the bottom side of a rectangular fabric piece 33 which is secured to an end of fabric strip 36, preferably by sewing as at 39. The toe end 52 of the horizontal fabric strip 36 has a button 40 sewn to its end, with a short section of the horizontal strip 36 having its outer sides folded together to form a vertical fold 42, by sewing the outer sides together. The outer sides are referenced as 46, 48 in FIG. 5, and create the vertical fold 42 of FIG. 6 after being sewn together.

Figures 8, 9:
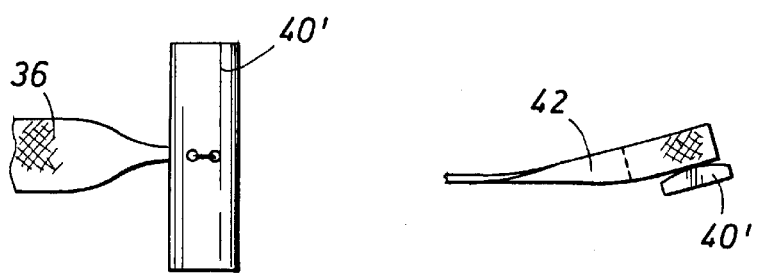
FIGS. 8 and 9 illustrate an alternative arrangement to that of FIGS. 5, 6, and 7 where a small flat rectangle is substituted for a button.

FIGS. 8 and 9 illustrate that a flat horizontal strip of plastic material 40' may be substituted for a round button 40.

Operation

When a foot drop patient goes to bed, he/she secures the leg member 12 about the lower portion of the leg 7 by wrapping the inner side 16 next to the leg 7 and with the loop section 20 attaching generally to the area A of hook section 18. The closing tab 22 may be loosely attached to the area C of hook section 18. The strap section 30 is not typically installed when the patient is in bed.

If the patient wants to get out of bed for a temporary trip to the toilet or kitchen or another room, he opens tab 22 and supports the toe end of this foot by placing the button 40 (or similar device such as tab 40') beneath his big toe and the adjacent toe with the vertical fold 42 extending through the space between the big toe and the adjacent toe. The patient attaches the loop section 32 of the strap against the hook section B facing outwardly from leg member 12 and then crosses the closing tab 22 about the fabric side 33 of the strap 30 with the loop section 24 attaching in the area C of hook section 18. The closing tab 22 secures the end of the strap 30 (that is loop section 32) in place while the tension of the strap maintained between toes and leg provides vertical support to the toe end 6 of the foot 5.

The patient reverses the step described above when he returns to bed by first releasing the closing tab 22 by pulling or "peeling" the loop 24 portion away from section C of hook portion 18, and then pulls or "peels" the loop portion 32 away from hook portion B. If desired, the patient removes leg member 12 by peeling the loop section 20 from hook section A of the leg member.

The invention finds use as a foot drop support arrangement for a barefoot person, but can also be used when a shoe is placed on the foot with the arrangement in place. Alternatively, the button 40 and strap 36 may be permanently secured to a shoe or sandal with the strap extending upwardly and backwardly from the toe of the shoe or sandal, where in operation the patient puts his/her foot into the shoe with the fold 42 extending between his toes.

Other fastening devices can be used in substitution for the hook and loop fastener of the preferred embodiment. For example, male and female snaps could be substituted, or eyelets and hooks, zippers, etc.

Other means for attaching the strap 36 to the patient's toes may also be used such as a loop that fits about the big toe of the foot.

Although the invention has been described above by reference to preferred embodiments, it should be understood that modifications to those embodiments may be within the scope of the invention as defined by the claims which follow.

What is claimed is:

1. A foot drop support arrangement comprising, a leg member (12) arranged and designed for removable securement about a lower leg, a strap (30) having a toe end and a leg end, with the toe end arranged and designed for support solely from a toe-end portion of a foot and a leg end arranged and designed for removable attachment to said leg member (12), whereby said arrangement provides support to said toe-end portion of said foot without support from a shoe, wherein said leg member (12) includes a first strip (14) having inner (16) and outer (15) sides having a section (18) of hook material attached to said outer (15) side at one end of the strip (14) and a first section (20) of loop material attached at the inner (20) side of said strip at the other end of the strip (14), said strip (14) being arranged and designed for said inner (16) side of said strip being wrapped about said leg with said first section of loop material (20) removably fastened to a portion (A) of said hook material (18), wherein said strap (30) includes a second strip (36) having a toe end and a leg end, with said toe end including means for support from a front portion of said foot and said leg end having a second loop section (32) attached thereto, and wherein said leg end of said strap (30) is removably secured to said leg member (12) when said leg member (12) is wrapped about said leg with said loop section (32) attached to a part (B) of said hook portion (18) of said first said strip (14), and said second strip (36) has a button secured at its toe end and with outer ends of said strip being folded and secured together to form a vertical fold.

2. The support arrangement of claim 1 wherein said leg member (12) includes a closing tab (22) secured to said other end of said strip (14), said closing tab (22) having a third section of loop material (24) arranged and designed for removable attachment to a third portion (C) of said hook portion (18).

3. A foot drop support arranged for a barefoot person comprising, a leg member (12) arranged and designed for removable securement about a lower leg, a strap (30) having, a toe end and a leg end with the toe end arranged and designed for support from a button (40) placed between a big toe shoe and an adjacent toe without any support from a shoe, and a leg end arranged and designed for removable attachment to said leg member (12), wherein said toe end of said strap (30) includes a strip (36) with said button (40) secured at said toe end and with outer ends of said toe end of said strip (36) being folded and secured together to form a vertical fold (42).

* * * * *